(12) United States Patent
Hallowitz et al.

(10) Patent No.: US 7,521,176 B2
(45) Date of Patent: Apr. 21, 2009

(54) METHODS FOR CHARACTERIZING THE VIRAL INFECTIVITY STATUS OF A HOST

(75) Inventors: Robert A Hallowitz, Aurora, CO (US); John Krowka, Frederick, MD (US); Shawn Matlock, Frederick, MD (US)

(73) Assignee: Theranostech, Inc., Albuquerque, NM (US)

( * ) Notice: Subject to any disclaimer, the term of this patent is extended or adjusted under 35 U.S.C. 154(b) by 1429 days.

(21) Appl. No.: 09/893,604

(22) Filed: Jun. 29, 2001

(65) Prior Publication Data

US 2002/0098476 A1 Jul. 25, 2002

Related U.S. Application Data

(63) Continuation-in-part of application No. 09/299,625, filed on Apr. 27, 1999, now Pat. No. 6,461,809, which is a continuation of application No. 09/139,663, filed as application No. PCT/US97/18649 on Oct. 15, 1997, now abandoned, and a continuation-in-part of application No. 08/732,782, filed on Oct. 15, 1996, now Pat. No. 5,817,458, which is a continuation-in-part of application No. 08/732,784, filed on Oct. 15, 1996, now Pat. No. 5,714,390.

(60) Provisional application No. 60/215,075, filed on Jun. 30, 2000, provisional application No. 60/083,078, filed on Apr. 27, 1998.

(51) Int. Cl.
*C12Q 1/70* (2006.01)
*G01N 33/53* (2006.01)

(52) U.S. Cl. .......................... 435/5; 435/7.1

(58) Field of Classification Search ............... 435/5, 435/7.1, 7.24, 388.3; 530/0.35, 0.75, 389.4, 530/0.6; 420/688.1, 208.1; 424/160.1, 154.1, 424/188.1, 208.1
See application file for complete search history.

(56) References Cited

U.S. PATENT DOCUMENTS 5,597,688 A * 1/1997 Connelly et al. ............... 435/5
5,817,458 A * 10/1998 King et al. .................. 435/5
2001/0008760 A1 * 7/2001 King et al. .................. 435/5

OTHER PUBLICATIONS

Gunthard, H. F., et al., 1999, "Evolution of envelope sequences of human immunodeficieny virus type 1 in cellular reservoirs i the setting of potent antiviral therapy", J. Virol. 73(11):9404-9412.*

Finzi, D., et al., 1999, "Latent infection of CD4+ T cells provides a mechanism for lifelong persistence of HIV-1, even in patients on effective combination therapy", Nat. Med. 5(5):512-.*
Gras, G., et al., 1993, "Complement and virus-specific antibody-dependent infection of normal B lymphocytes by human immunodeficiency virus type 1", Blood 81(7):1808-1818.*
Mercure, L., et al., 1993, "Detection of unintegrated human immunodeficiency virus type 1 DNA in persistently infected CD8+ cells", J. Gen. Virol. 74:2077-2083.*
Strongin, W., 1992, "Sensitivity, specificity, and predictive value of diagnostic tests: definitions and clinical applications", in Laboratory Diagnosis of Viral Infections, Second Edition, Lennette, E. H., ed., Marcel Dekker, Inc., pp. 211-219.*
Zolla-Pazner, S., et al., 1995, "Serotyping of primary human immunodeficiency virus type 1 isolates from diverse geographic locations by flow cytometry", J. Virol. 69(6):3807-3815.*
Pedersen, C., et al., 1992, "The effect of treatment with zidovudine with or without acyclovir on HIV p24 antigenaemia in patien with AIDS or AIDS-related complex", AIDS 6:821-825.*
Molina, J.-M., et al., 1994, "Quantification of HIV-1 virus load under zidovudine therapy in patients with symptomatic HIV infection: relation to disease progression", AIDS 8:27-33.*
Bottarel, F., et al., 1999, "The cell death-inducing ability of glycoprotein 120 from different HIV strains correlates with their abilit to induce CD4 lateral association with CD95 on CD4+ T cells", AIDS Res. Human Retrovir. 15(14):1255-1263.*
Zolla-Pazner, S., et al. Jun. 1995. Serotyping or primary human immunodeficiency virus type 1 isolates from diverse geographical locations by flow cytometry. J. Virol. 69(6):3807-3815.*
Daneil, V., et al., 1993, Association of T cell and macrophage dysfunction with surface gp120-immunoglobulin-complement complexes in HIV-infected patients, Clin. Exp. Immunol. 93:152-156.*
Cummings, R. T., et al., 1999, Use of a phosphotyrosine-antibody pair as a general detection method in homogenous time-resolved fluorescence: application to human immunodeficiency viral protease, Anal. Biochem. 269:79-93.*
Reichelderfer, P.S., "Laboratory Monitoring of the Viral Life Cycle", 1998, Conference on the Laboratory Science of HIV, Sep. 16, 1998, p. 11-17.

* cited by examiner

*Primary Examiner*—J. S. Parkin
(74) *Attorney, Agent, or Firm*—V. Gerald Grafe

(57) ABSTRACT

Methods in accordance with the present invention involve novel measurements of the disease status of hosts infected with the human immunodeficiency virus. In particular, the present invention relates to a measurements of the numbers in a sample volume of (a) productively HIV-infected cells and (b) cells capable of being infected by HIV, e.g., cells expressing CD4, CCR5, and/or CXCR4. These two values can be represented as a single ratio, e.g., number of productively infected cells/number of cells capable of being infected by HIV, and can be utilized as an indicator of disease status, such as disease progression, viral replication, etc.

5 Claims, No Drawings

METHODS FOR CHARACTERIZING THE VIRAL INFECTIVITY STATUS OF A HOST

This application claims the benefit of U.S. Provisional Application Ser. No. 60/215,075, filed on Jun. 30, 2000, incorporated herein by reference; and, as a continuation-in-part, to U.S. Pat. No. 6,461,809, "Methods of improving infectivity of cells for viruses," Ser. No. 09/299,625 filed Apr. 27, 1999 and issued Oct. 8, 2002; which claimed the benefit of U.S. Provisional Application Ser. No. 60/083,078, filed Apr. 27, 1998; and which is a continuation of Ser. No. 09/139,663 filed Aug. 25, 1998 now abandoned which is a 371 of PCT/US97/18649, filed Oct. 15, 1997, which is a continuation-in-part of U.S. Ser. No. 08/732,782, filed Oct. 15, 1996, now U.S. Pat. No. 5,817,458, and U.S. Ser. No. 08/732,784, filed Oct. 15, 1996, now U.S. Pat. No. 5,714,390, all of which are incorporated by reference herein.

DESCRIPTION OF THE INVENTION

Cells infected with human immunodeficiency virus (HIV) display a number of characteristics features of viral infection, including the expression of viral antigens, reverse transcriptase, nucleic acids coding for virus, reduced numbers of circulating CD4 positive T-cells, etc. See, e.g., *Current Medical Diagnosis and Treatment*, Chapter 31, Tierney et al., eds., 39th Edition, McGraw-Hill, 2000. The present invention relates to compositions and methods for treating, diagnosing, assessing the status of, etc., hosts infected with (HIV) which utilize these and other characteristics of viral infection.

Methods in accordance with the present invention involve novel measurements of the disease status of hosts infected with the human immunodeficiency virus. In particular, the present invention relates to a measurements of the numbers in a sample volume of (a) productively HIV-infected cells and (b) cells capable of being infected by HIV, e.g., cells expressing CD4, CCR5, and/or CXCR4. These two values can be represented as a single ratio, e.g., number of productively infected cells/number of cells capable of being infected by HIV, and can be utilized as an indicator of disease status, such as disease progression, viral replication, etc. As explained below, the aforementioned ratio is useful for characterizing the disease status of an infected host and designing regimes which are effective to treat the HIV infection. The ratio can be used in combination with other characteristics of HIV infection, including, e.g., viral load (e.g., as measured by RT-PCR), plasma levels of reverse transcriptase and/or HIV nucleic acid, presence of viral antigens, such as p24, presence of gag-pol RNA, CD45RO count, etc.

An aspect of the invention relates to methods of assessing the "infectivity status" of a host infected with HIV, comprising, e.g., measuring the number of productively-infected cells and the number of cells which are capable of being infected by HIV, whereby the infectivity status of the host is assessed. These fractions can be presented as a ratio, e.g., the number of cells per unit volume which express cell-surface gp120 (productively-infected cells) divided by the number of cells per unit volume which are CD4 positive (cells capable of being HIV-infected).

The phrase "infectivity status" is intended as a description of the condition of a host with respect to the HIV virus, e.g., how many cells are actually infected with the HIV virus in comparison to the total number of cells which are capable of being infected. Such a value can be used to accurately describe the disease status of a patient, and determine the efficacy of treatment. Heretofore, CD4 and viral RNA markers (e.g., pol or gag) have been used as surrogates for assessing the disease status of a patient and the efficacy of treatment. However, CD4 positive cell counts have remained low in some patients, despite low levels of plasma RNA virus. See, e.g., Patterson et al., Lancet, 353:211-212, 1999. Thus, viral RNA is not always a good indicator of disease or treatment efficacy. A gp120/CD4 positive cell ratio in accordance with the present invention provides a superior value for assessing patient treatment and HIV disease progression. For example, a patient who had been shown to have low systemic CD4 positive cells and low RNA virus, may have measurable numbers of gp120 positive cells, indicating that HAART (highly active antiretroviral therapy) therapy should be continued. If this patient had been receiving, e.g., a protease inhibitor and two reverse transcriptase inhibitors, the detection of measurable numbers of gp120 cells indicates that the viral infection is continuing, and that the HAART therapy should be increased, e.g., by increasing dosages and/or by adding additional antiretroviral agents.

A "productively infected" cell means a cell which is infected by the HIV virus and which is actively producing functional virus. Any marker associated with the viral replication cycle can be used to measure productively infected cells, such as the presence of cell-associated viral RNA or antigens. Assays for each class of markers are well-known. For instance, viral RNA can be measured by branched DNA (bDNA) signal amplification [C. Pachl et al., "Rapid and precise quantification of HIV-1 RNA in plasma using a branched DNA (bDNA) signal amplification assay," *J. Acquir. Immune Def. Snydrome Hum. Retrovirol.*, 8:446-454 (1995); D. Kern et al., "An enhanced sensitivity branched DNA assay for quantification of human immunodeficiency virus type 1 RNA in plasma," *J. Clin. Microbiol.*, 34:3196-3202 (1996)], RT-PCR [K. B. Mullis et al., "Specific synthesis of DNA in vitrovia a polymerase-catalyzed chain reaction," *Methods Enzymol.*, 155:335-350 (1987); R. K. Saiki et al., "Primer-directed enzymatic amplification of DNA with a thermostable DNA polymerase," *Science*, 239:487-491 (1988)], QC-PCR [M. J. Piatak et al., "High levels of HIV-1 in plasma during all stages of infection determined by competitive PCR, " *Science*, 259:1749-1754 (1993); M. J. Piatak et al., "Quantitative competitive polymerase chain reaction for accurate quantitation of HIV DNA and RNA species," *BioTechniques*, 14:70-79 (1993)], or nucleic acid sequence based amplification ("NASBA") [B. van Gemen et al., "Quantification of HIV-1 RNA in plasma using NASBA TM during HIV-1 primary infection," *J. Virol. Methods*, 43:177-188 (1993)]. See, also, e.g., *The AIDS Knowledge*, Chapter 2.4, "Viral Load Assays," published 1998 (http://kali.ucsf.edu/akb/1997/02qrna/index.html). Polypeptide antigens that can be utilized a markers for productive infection, include, e.g., gp120, gp41, and p24. p24 can be measured according to any effective assay, e.g., ELISA or Western blot. Assays for p24 can be performed as described in, e.g., *The AIDS Knowledge*, Chapter 2.3 "Tests to Detect HIV Antigen," published 1998 (http://kali.ucsf.edu/akb/1997/02agtest/index.html), [J. Mckeating, "Quantitative assays for virus neutralization," In: Karn J., ed. HIV: A practical approach," *Virology and Immunology*, vol. 1. Oxford: IRL Press at Oxford University Press, pp. 118-127 (1995); P. Nishanian et al., "A simple method for improved assay demonstrates that p24 antigen is present as immune complexes in most sera from infected individuals," *J. Infect. Dis.*, 162:21-28 (1990); AABB Association Bulletin #96-2: HIV-1 antigen Test Implementation Guidance, Jan. 5, 1996]. Productively infected cells can also be determined by quantitative coculture of peripheral blood mononuclear. This assay measures the number of HIV infected cells in a sample by determining the ability of sample cells to infect naive, uninfected cells. See, e.g., Hollinger et al, *J. Clin. Micro.,* 30:1787-1794, 1992.

In preferred embodiments of the present invention, the number of productively-infected cells in a sample is determined by the presence of cell-associated gp120. gp120 as a marker for productively infected cells has unexpected advantages over other assays and markers. For instance, gp 120 provides higher accuracy and ease of measurement than viral nucleic acid markers, such as those measured by PCR-based assays, quantitative coculture, and assays for other protein antigens, such as p24. In addition, gp120 is a more reliable measure of productive infection since it is a functional marker of viral replication. Nucleic acid-based assays, for instance, detect functional and non-functional, defective virus, giving misleading information about whether active infection is ongoing.

Cell-associated gp120 is can be measured by any effective assay. For instance, cells bearing cell-surface gp120 can be counted by labeling cells with an immunofluorescent marker, such as FITC, PE, or rhodamine, followed by counting the labeled cells, e.g., using a flow cytometer, on a hemocytometer, etc. Prior to counting, the cells can be separated, e.g., by magnetic separation techniques, e.g., as described in U.S. Pat. No. 5,817,458. An assay for cell-surface gp120 can comprises one or more of the following steps in any effective order: combining an effective amount of an anti-gp120 antibody attached to a detectable label, an effective amount of an antibody specific-for said detectable label, and an aqueous sample containing viral-infected cells displaying said gp120 to form a mixture, wherein said antibody specific-for said detectable label is attached to a magnetic particle; incubating said mixture under conditions effective for binding of said anti-gp120 antibody to gp120 on said cells, and, for binding of said antibody specific-for said detectable label to said detectable label attached to said anti-gp120 antibody, to form a complex, wherein said anti-gp120 antibody is bound to said gp120 displayed on a viral-infected cell; separating said complex by applying a magnetic field to said mixture, whereby said complex is retained by said magnetic field, and determining the presence of magnetically-separated cells by detecting said detectable label, whereby said magnetically separated cells are peripheral blood mononuclear cells expressing cell-surface gp120. Such an assay is described in U.S. application Ser. No. 09/139,663.

The cells which are "capable of being infected by HIV" means, e.g., cells which express on their cell-surface the antigens which are utilized by the HIV virus to latch on to the cell in order to enter it. These antigens include, e.g., CD4, chemokine receptors, CCR5, CXCR4, CCR3, CCR2b, Bonzo, STRL33, BOB, GPR15, GPR1, US28, etc. See, e.g., *Nature,* 388:230-231, 1997; *J. Virol.,* 71:1657-1661, 1997; Dean et al., *Science,* 273:1856-1862, 1996; E. A. Berger, 1997, AIDS, 11:S3-S16; Broder et al., 1997, *J. Leukocyte Biol.,* 62:20-29; Doms et al., 1997, *Virology,* 235:279-190; and Moore et al., 1997, *Curr. Opinion Immunol.,* 9:551-562. CD4 can be used alone, or in combination with any other antigen, such as a chemokine receptor, e.g., CCR5 or CXCR4.

CD4+ cells can be measured by any suitable means. For example, CD4 counts can be determined by immunotyping where detection of antigenic determinants specific to cell types is accomplished using labeled antibodies and generally a flow cytometer. These methods are widely utilized. See, e.g., 1997 Revised Guidelines for Performing CD4+ T-Cell Determinations in Persons Infected with Human Immunodeficiency Virus (HIV); Johnson et al., J. Acquired Imm. Def., 10:522-530, 1995.

Generally, immunotyping for the presence of CD4+ cells involves labeling cells with appropriate combinations of antibodies to distinguish CD4 T-cells from CD8 T-cells. CD4 T-cells can be identified as being positive for both CD3 and CD4; CD8 T-cells can be identified as being positive for both CD3 and CD8. CD45 can be further included to ensure that only lymphocytes are included. Two-, three- (Mercolino et al., Cytometry, 22:48-59, 1995; Nicholson et al., Cytometry, 26:227-230, 1996), or four-color assays can be utilized. CD3 can be used as common lineage marker for all lymphoctes, where other markers can used to distinguish other classes, such as those mentioned above, and CD19 for B-cells; CD16 for NK cells, granulocytes, and macrophages; CD56 for NK cells.

If a sample is whole blood, it may be desirable to treat or fractionate the sample prior to determining the number of CD4 positive and/or productively-infected cells. Whole blood comprises, e.g., serum, proteins, erythrocytes, leucocytes, platelets, etc. The leucocyte fraction includes, polymorphonuclear granulocytes, monocytes, and lymphocytes. The erythrocytes can be lysed by any conventional method, such as using ammonium chloride.

The samples can be stained and fixed by conventional methods, and then immunotyped. If desired, the peripheral blood mononuclear cells ("PBMC", e.g., monocytes and lymphocytes) are separated from the whole blood using a centrifugation procedure with an appropriate medium, such as Lymphocyte Separation Medium (ICN—Costa, Mesa, Calif.).

As mentioned, a preferred ratio in accordance with the present invention Comprises. the number of gp120 positive cells per unit volume/the number of CD4 positive cells per unit volume. The determination of gp120-bearing cells can be made on the same or different sample as the one use to determine CD4+ cells. The number of CD4-bearing cells can be determined by the immunotyping procedures as described above.

During HIV infection, CD4 bearing cells can be underestimated because the CD4 antigen can be down-regulated in infected, or cells which have acquired gp120 from the plasma. Thus, in certain aspects of the invention, the CD4 positive count can be determined by measuring CD4 positive cells and then adding to it cells which are expressing gp120 antigen on their cell-surface. Such count can be referred herein as the "adjusted CD4 positive cell count."

Pools of receptive cells, and subsets of these pools which are infected with virus, can be determined in various ways. As described above, CD4 and gp120 expression are determined independently of each other. For example, the antigens can be labeled with different markers (e.g., using a FITC-conjugated antibody for a first antigen, and a rhodamine-conjugated antibody for a second antigen), and then examined for the presence of each marker.

Fluorescence resonance energy transfer ("FRET") systems can also be used to determine co-expression of a viral antigen and a cellular antigen present on viral receptive cells. In a FRET assay, an excited donor fluorophore transfers its energy to an acceptor fluorophore when the two are in proximity. This transfer is not an emission and absorption of light, but a non-radiative, direct energy transfer. The emission of a detectable signal from the acceptor molecule indicates it is close to the donor. By labeling antibody types with different acceptor and donor flurophores, it can be determined when the antibodies are recognized antigens which are co-expressed in the same cell. For instance, if anti-HIV antigen (e.g., anti-gp120) is labeled with a donor, and a cell-based antigen (e.g., CD4, CD45, etc.) is labeled with an acceptor, a FRET assay can be used to determine when both antigens are present on the same cell, or when only one antigen is present. In the latter case, the donor and acceptor molecules would have detectable signals which are different from the signal produced when the donor is in close proximity to the acceptor. There are many commercially available systems.

A suitable system for the present invention uses Renilla luciferase (Rluc) as the donor and a modified Green Fluorescent Protein (GFP2) as the acceptor molecule in an assay analogous to fluorescence resonance energy transfer (FRET), but without the need for an excitation light source. Rluc emits blue light between 390-400 nm upon addition of the substrate, DeepBlueC™. GFP2 absorbs this light and emits fluorescence at 505-510 nm that can be detected using a fluorimeter. If Rluc and GFP2 are in close proximity, due to binding of the biological partners, energy is efficiently transferred and both the blue light of Rluc and green light of GFP2 are detected. See, e.g., Xu et al., *Proc. Natl. Acad. Sci.*, 96:151-6, 1999; Angers et al., *Proc. Natl. Acad. Sci.*, 97:3684-9, 2000. Another commercially available technology that can be used is AlphaScreen™, an "Amplified Luminescent Proximity Homogeneous Assay" method. Upon illumination with laser light at 680 nm, a photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity of the donor bead, by virtue of a biological interaction, the singlet-state oxygen molecules reacts with chemiluminescent groups in the acceptor beads, which immediately transfer energy to fluorescent acceptors in the same bead. These fluorescent acceptors shift the emission wavelength to 520-620 nm. The whole reaction has a 0.3 second half-life of decay, so measurement can take place in time-resolved mode. For other flourophores, e.g., Carraway et al., *J. Biol. Chem.* 264(15):8699-707, 1989; green fluorescent protein and acceptor fluorophore Cy3. Donor and acceptor fluorophores can be routinely coupled to the appropriate antibody.

EXAMPLES

Methods

Studies made to establish sensitivity, specificity, positive predictive value, and accuracy (as compared with HIV culture) were performed in 62 patients who were known to be seropositive for HIV-1 and were in various stages of the HIV disease process. Almost all were homosexual men between ages 25 and 65. Most of the subjects were taking antiretroviral therapy, some were about to commence therapy.

Clinical application was explored in a group of 45 patients within one clinical trial that compared the outcomes of HAART that comprised 3 drugs with those from HAART that comprised 4 drugs.

The false positive rate was studied in 70 putatively HIV-negative individuals; these were recruited from among patients attending the Department of Medicine and from among members of the clinic staff. These were all presumed by the investigators to be HIV-negative and did not announce themselves to be HIV-positive when invited to participate as HIV-negative controls; we did not perform HIV antibody or antigen tests in these persons blood samples.

Three different monoclonal antibodies (Mabs) against HIV-1 gp120 were commercially obtained and were conjugated with fluorescein isothiacyanate. These three Mabs, used in combination, were identified as the optima amongst many that were tried both singly and in various combinations. The three were used in combination for labeling the lymphocytes.

Labeling of cells for flow cytometric analysis was conducted according to CDC guidelines for immunophenotyping assays. Whole blood was collected in EDTA, maintained at 18-22° C. during transport, and testing was performed within 30 hours of the blood draw.

Flow cytometric analysis was made on a Becton Dickinson FACSCalibur flow cytometer using CELLQuest acquisition and statistical analysis software. Results were expressed as % of CD4+ cells expressing gp120 (gp120+/CD4+). ROC curves established $\geq$10% gp120+/CD4+ as the cut-off for defining a positive test.

Quantitative PBMC micro co-culture was made by the ACTG consensus protocol which uses limiting dilution culture data with a maximum likelihood method (DAIDS Virology Manual for HIV Laboratories, version Jan. 1, 1997). Results are expressed as infectious units per million cells (IUPM).

The studies were approved by the Institutional Review Board and all subjects, both HIV-positive individuals and putatively HIV-negative persons, gave signed, informed consent.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above, including U.S. application Ser. No. 09/139,663 and PCT/US97/19849, are hereby incorporated by reference. U.S. Provisional Application Ser. No. 60/215,075, filed Jun. 30, 2001, is hereby incorporated by reference in its entirety From the foregoing description, one skilled in the art can easily ascertain the essential characteristics of this invention, and without departing from the spirit and scope thereof, can make various changes and modifications of the invention to adapt it to various usages and conditions.

We claim:

1. A method of detecting lymphocytes expressing cell-surface gp120 in an aqueous sample containing viral infected cells displaying gp120, comprising:
   a. combining to form a mixture:
      i. an effective amount of a plurality of monoclonal antibodies, each specific to a different epitope of gp120, wherein each such monoclonal antibody is attached to one of one or more detectable labels,
      ii. an effective amount of one or more second antibodies, each comprising an antibody specific for one or more of said detectable labels, wherein each of said second antibodies is attached to a magnetic particle, and
      iii. the sample;
   b. incubating said mixture under conditions effective for (i) binding of said monoclonal antibodies to gp120 on said cells, and (ii) for binding of said second antibodies to said detectable labels attached to said monoclonal antibodies, to form a complex, wherein each of said monoclonal antibodies is bound to said gp120 displayed on a viral infected cell;

c. separating said complex by applying a magnetic field to said mixture, whereby said complex is retained by said magnetic field, and d. determining the presence of magnetically separated lymphocytes expressing cell-surface gp120.

2. A method as in claim 1, wherein step (d) comprises counting the number of cells attached to the one or more detectable labels.

3. A method as in claim 2, wherein counting the number of cells comprises detecting complexes that emit light at one or more predetermined wavelengths in response to incident radiation.

4. A method as in claim 3, wherein counting the number of cells comprises using flow cytometry.

5. A method as in claim 3, wherein counting the number of cells comprises using fluorescence microscopy.

* * * * *